United States Patent
Warpehoski et al.

(10) Patent No.: US 6,437,177 B1
(45) Date of Patent: *Aug. 20, 2002

(54) α-HYDROXY, -AMINO, AND HALO DERIVATIVES OF β-SULFONYL HYDROXAMIC ACIDS AS MATRIX METALLOPROPTEINASES INHIBITORS

(76) Inventors: Martha A. Warpehoski, 7600 Curry La., Portage, MI (US) 49024; Mark Allen Mitchell, 1628 Dover Rd., Kalamazoo, MI (US) 49008; Donald E. Harper, 11520 Channel Dr., Plainwell, MI (US) 49080; Linda Louise Maggiora, 4400 Glenrose Ter., Kalamazoo, MI (US) 49008

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/196,190

(22) Filed: Nov. 20, 1998

Related U.S. Application Data
(60) Provisional application No. 60/072,655, filed on Nov. 21, 1997.

(51) Int. Cl.$^7$ .................. C07C 317/04; A61P 11/06
(52) U.S. Cl. .................. 562/426; 562/470; 562/496; 562/508; 562/581; 562/605
(58) Field of Search .................. 562/621, 623, 562/400, 426, 503, 504, 505, 506, 507, 470, 496, 508, 581, 605; 514/568

(56) References Cited

U.S. PATENT DOCUMENTS

| | | | |
|---|---|---|---|
| 5,847,153 A | * 12/1998 | Warpehoski et al. | 548/319.5 |
| 5,932,595 A | * 8/1999 | Bender et al. | 514/317 |

FOREIGN PATENT DOCUMENTS

| EP | 0 780 386 | | 6/1997 |
|---|---|---|---|
| WO | WO 97/24117 | | 7/1997 |
| WO | WO 97/49679 | | 12/1997 |
| WO | WO 98/05635 | | 2/1998 |
| WO | WO 98/13340 | | 4/1998 |
| WO | WO 98/34915 | | 8/1998 |
| WO | WO 98/39326 | * | 9/1998 |

OTHER PUBLICATIONS

Boyle et al., Xenobiotica, 23(7), pp. 781–798, 1993.*
Griffith, Methods Enzymol., pp. 274–279, 1987.*
Bayer et al., J. Chromatogr., 320(2), pp. 393–396, 1985.*
Bredereck et al., Chem. Ber. 93, pp. 2415–2423. Chemical abstracts 55:2545c is substituted, 1960.*
U.S. patent application Ser. No. 09/355,315, filed Jul. 30, 1999, pending.
U.S. patent application Ser. No. 09/269,185, filed Mar. 29, 1999, pending.
U.S. patent application Ser. No. 09/196,190, filed Nov. 20, 1998, pending.
U.S. patent application Ser. No. 09/530,965, filed May 18, 2000, pending.

* cited by examiner

Primary Examiner—Mukund J. Shah
Assistant Examiner—Thomas McKenzie
(74) Attorney, Agent, or Firm—Oblon, Spivak, McClelland, Maier & Neustadt, P.C.

(57) ABSTRACT

The present invention provides a compound of formula I

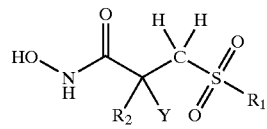

or pharmaceutical acceptable salts thereof wherein $R_1$ is $C_{4-12}$ alkyl, $C_{4-12}$ alkenyl, $C_{4-12}$ alkynyl, $-(CH_2)_h-C_{3-8}$ cycloalkyl, substituted and unsubstituted $-(CH_2)_h$-aryl, substituted and unsubstituted $-(CH_2)_h$-het, $R_2$ is substituted and unsubstituted $C_{1-12}$ alkyl, substituted and unsubstituted $C_{2-12}$ alkenyl, substituted and unsubstituted $C_{2-12}$ alkynyl, substituted and unsubstituted $-(CH_2)_h-C_{3-8}$ cycloalkyl, substituted and unsubstituted $-(CH_2)_h-C_{3-8}$ cycloalkenyl, substituted and unsubstituted $-(CH_2)_h$-aryl, substituted and unsubstituted $-(CH_2)_h$-heterocyclic ring, substituted and unsubstituted $-(CH_2)_i-X-R_4$ (X is $-O-$, $-S(=O)_j-$, $-NR_7-$, $-S(=O)_2NR_8-$, or $-C(=O)-$), and $-(CH_2)_i CHR_5R_6$.

The compounds are inhibitors of matrix metalloproteinases involved in tissue degradation.

13 Claims, No Drawings

α-HYDROXY, -AMINO, AND HALO DERIVATIVES OF β-SULFONYL HYDROXAMIC ACIDS AS MATRIX METALLOPROPTEINASES INHIBITORS

This application claims priority to U.S. Provisional Application Serial No. 60/072,655, filed on Nov. 21, 1997.

FIELD OF THE INVENTION

The present invention relates to novel α-hydroxy, amino, and halo derivatives of β-sulfonyl hydroxamic acids, to pharmaceutical compositions containing them, and to the method of using them. The compounds of the invention are inhibitors of matrix metalloproteinases involved in tissue degradation.

BACKGROUND OF THE INVENTION

Loss of connective tissue integrity occurs in many disease processes, including osteoarthritis, rheumatoid arthritis, septic arthritis, osteopenias such as osteoporosis, tumor metastasis (invasion and growth), periodontitis, gingivitis, corneal ulceration, dermal ulceration, gastric ulceration, inflammation, asthma and other diseases related to connective tissue degradation. Although there is a high incidence of these diseases in the developed world, there is no treatment that prevents the tissue damage that occurs. Considerable lines of scientific evidence indicate that uncontrolled connective matrix metalloproteinase (MMPs) activity is responsible for the damage, and as a consequence the inhibition of these enzymes has become the target for therapeutic intervention (see Matrisian, L. M., Bases, Vol. 14, pp 445–463 (1992); Emonard, H. et al., Cellular and Molecular Biology, Vol. 36, pp 131–153 (1990); Docherty, A J. P. et al., Annals of the Rheumatic, Vol. 49, pp 469–479 (1990)).

Hydroxamic acid derivatives are a class of known therapeutically active MMPs inhibitors and there are numerous references in the art disclosing a variety of hydroxamic acid derivatives. For example, European Patent Publication No. 0,606,046 A1 discloses arylsulfonamido-substituted hydroxamic acids useful as matrix metalloproteinase inhibitors. International Publication Nos. WO 95/35275 and WO 95/35276 disclose sulfonamide hydroxamic acid and carboxylic acid derivatives useful as matrix metalloproteinases inhibitors. All these references relate to sulfonamide hydroxamic acids. The compounds of this invention are novel and distinct from all other sulfonamide hydroxamic acids in that the usual nitrogen atom is replaced by a carbon atom. The invention provides sulfonyl hydroxamic acid derivatives.

The compounds of the present invention inhibit various enzymes from the matrix metalloproteinase family, predominantly stromelysin and gelatinase, and hence are useful for the treatment of matrix metallo endoproteinase diseases such as osteoporosis, tumor metastasis (invasion and growth), periodontitis, gingivitis, corneal ulceration, dermal ulceration, gastric ulceration, inflammation, asthma, and other diseases related to connective tissue degradation.

INFORMATION DISCLOSURE

The European Patent Application No. EP 0780 386 A1 discloses matrix metalloproteinases inhibitors useful in the treatment of mammals having disease states alleviated by the inhibition of such matrix metalloproteinases.

International Publication No. WO 97/24117 discloses substituted aryl, heteroaryl, arylmethyl or heteroarylmethyl hydroxamic acid compounds especially useful for inhibiting the production or physiological effects of TNF in the treatment of a patient suffering from a disease state associated with a physiologically detrimental excess of tumor necrosis factor (TNF).

International Patent Application No. PCT/US97/16348 discloses β-sulfonyl hydroxamic acids as matrix metalloproteinases inhibitors.

The compounds of the present invention are novel and distinct from the above hydroxamic acids in that they have a hydroxy, amino group or fluoro on the α-position and two hydrogen atoms at the β-position of the hydroxmate group.

SUMMARY OF THE INVENTION

The present invention provides novel compounds of formula I

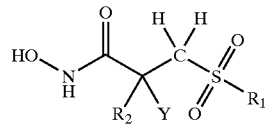

or pharmaceutical acceptable salts thereof wherein:

$R_1$ is
a) $C_{4-12}$ alkyl,
b) $C_{4-12}$ alkenyl,
c) $C_{4-12}$ alkynyl,
d) —$(CH_2)_h$—$C_{3-8}$ cycloalkyl,
e) —$(CH_2)_h$-aryl,
f) —$(CH_2)_h$-aryl substituted with $C_{1-4}$ alkyl, $C_{1-4}$ alkoxy, phenyl, $C_{1-4}$ phenoxy, het, halo, —$NO_2$, —$CF_3$, —CN, or —$N(C_{1-4}$ alkyl$)_2$,
g) —$(CH_2)_h$-het, or
h) —$(CH_2)_h$-het substituted with $C_{1-4}$ aLkyl, phenyl, $C_{1-4}$ phenoxy, het, or halo;

$R_2$ is
a) $C_{1-2}$ alkyl,
b) $C_{1-2}$ alkyl substituted with one to three halo, —CN, —$NO_2$, —$CF_3$, —$N(R_3)_2$, —$SR_3$, or OH,
c) $C_{2-12}$ alkenyl,
d) $C_{2-12}$ alkenyl substituted with one to three halo, —CN, —$NO_2$, or —$CF_3$,
e) $C_{2-12}$ alkynyl,
f) $C_{2-12}$ alkynyl substituted with one to three halo, —CN, —$NO_2$, or —$CF_3$,
g) —$(CH_2)_h$—$C_{3-8}$ cycloalkyl,
h) —$(CH_2)_h$—$C_{3-8}$ cycloalkyl substituted with one to three $C_{1-4}$ alkyl, $C_{1-4}$ alkoxy, or halo,
i) —$(CH_2)_h$—$C_{3-8}$ cycloalkenyl,
j) —$(CH_2)_h$—$C_{3-8}$ cycloalkenyl substituted with one to three $C_{1-4}$ alkyl, $C_{1-4}$ alkoxy, or halo,
k) —$(CH_2)_h$-aryl,
l) —$(CH_2)_h$-aryl substituted with one to three $C_{1-4}$ alkyl, $C_{1-4}$ alkoxy, —$CF_3$—OH, —$NO_2$, —CN, —$N(R_3)_2$, —$SR_3$, —$SO_2(C_{1-4}$ alkoxy), —C(=O)$R_3$, or —NC(=O)$R_3$,
m) —$(CH_2)_h$-aryl substituted with one to five halo,
n) —$(CH_2)_h$-het,
o) —$(CH_2)_h$-het substituted with one to two $C_{1-4}$ alkyl, or halo,
p) —$(CH_2)_h$—Q,
q) —$(CH_2)_h$—Q substituted with one to three $C_{1-4}$ alkyl, $C_{1-4}$ alkoxy, halo, or phenyl,
r) —$(CH_2)_i$—X—$R_4$, optionally the —$(CH_2)_i$— chain can be substituted withg one to with $C_{1-4}$ alkyl or phenyl, which in turn can be substituted with one to three halo or $C_{1-4}$ alkyl, or s) $—(CH_2)_nCHR_5R_6$;

$R_3$ is
a) H,
b) $C_{3-6}$ cycloalkyl,
c) $C_{1-4}$ alkyl,
d) $—(CH_2)_n$-phenyl, or
e) $—(CH_2)_n$-phenyl substituted with one to three $C_{1-4}$ alkyl, $C_{1-4}$ alkoxy, or halo;

X is
a) —O—,
b) —S(=O)$_j$—,
c) —NR$_7$—,
d) —S(=O)$_2$NR$_8$—, or
e) —C(=O)—;

$R_4$ is
a) H,
b) $C_{1-8}$ alkyl,
c) $—(CH_2)_n$-phenyl,
d) $—(CH_2)_n$-phenyl substituted with one to three $C_{1-4}$ alkyl, $C_{1-4}$ alkoxy, phenyl, $C_{1-4}$ phenoxy, het, halo, —NO$_2$, or —CN, or
e) $—(CH_2)_n$-het;

$R_5$ is
a) $C_{1-4}$ alkyl, or
b) —C(=O)R$_3$;

$R_6$ is
a) —C(=O)R$_3$, or
b) $—(CH_2)_nC(=O)R_3$;

$R_7$ is
a) H,
b) $C_{1-4}$ alkyl,
c) $—(CH_2)_n$-phenyl,
d) $—(CH_2)_n$-phenyl substituted with one to three $C_{1-4}$ alkyl, $C_{1-4}$ alkoxy, or halo,
e) —(C(=O)—R$_3$,
f) —S(=O)$_2$R$_3$, or
g) —C(=O)OR$_3$;

$R_8$ is
a) $C_{1-4}$ alkyl,
b) $—(CH_2)_n$-phenyl, or
c) $—(CH_2)_n$-phenyl substituted with one to three $C_{1-4}$ alkyl, $C_{1-4}$ alkoxy, or halo;

Y is
a) —OH,
b) —NR$_9$R$_{10}$, or
c) fluoro;

$R_9$ and $R_{10}$ are the same and different and are
a) H,
b) —C(=O)—R$_3$,
c) —C(=O)—OR$_3$, or
d) —C(=O)—NHR$_3$;

aryl is monocarbocyclic, or bicarbocyclic aromatic moiety;

het is 5- to 10-membered unsaturated monomonocyclic or bicyclic heterocyclic moiety having one to three atoms selected from the group consisting of oxygen, nitrogen, and sulfur;

Q is 5- to 10-membered saturated monocyclic or bicyclic heterocyclic moiety having one to two atoms selected from the group consisting of oxygen, nitrogen, and sulfur; aryl, het, $C_{,1-12}$ alkyl, $C_{1-4}$ alkyl $C_{2-12}$ alkenyl, $C_{2-12}$ alkynyl, $—C_{3-8}$ cycloalkyl, $—C_{3-6}$ cycloalkenyl, and phenyl being optionally substituted; h is 0, 1, 2, 3, 4, 5, or 6; i is 1, 2, 3, 4, 5, 6, 7, 8, 9, or 10; j is 0, 1, or 2; and with the following provisos: a) where $R_2$ is $C_{1-6}$ alkyl, Y is other than —NR$_9$R$_{10}$, b) where h is 0, het and Q are attached to the α-position via carbon atom of heterocyclic moiety.

The compounds of the present invention inhibit various enzymes from the matrix metalloproteinase family, predominantly stromelysin and gelatinase, and hence are useful for the treatment of matrix metallo endoproteinase diseases.

As stated above, aryl, het, $C_{1-4}$ alkyl, $C_{1-12}$alkyl, $C_{2-12}$ alkenyl, $C_{2-12}$ alkynyl, $—C_{3-8}$ cycloalkyl, $—C_{3-8}$ cycloalkenyl, Q and phenyl may be substituted as appropriate. Aryl is preferably substituted with $C_{1-4}$ alkyl, $C_{1-4}$ alkoxy, phenyl, O-phenyl, het, O-het, halo such as fluoro, chloro, bromo, OH, —NO$_2$, —CN, —CF$_3$, —N(R$_3$)$_2$ such as —N(C$_{1-4}$ alkyl)$_2$, —SR$_3$, —SO$_2$(C$_{1-4}$ alkoxy), —(CH$_2$)$_n$-het; —C(=O)R$_3$ or —NHC(=O)R$_3$; het is preferably substituted with $C_{1-4}$ alkyl, pheny, phenoxy or halo; $C_{1-12}$ alkyl is preferably substituted with one to three halo, CN, —NO$_2$ or CF$_3$; N(R$_3$)$_2$ such as —N(C$_{1-4}$ alkyl)$_2$, —SR$_3$ or —OH; $C_{2-12}$ alkenyl, and $C_{2-12}$ alkynyl are preferably substituted with one to three halo, CN, —NO$_2$ or —CF$_3$; $C_{3-8}$ cycloalkyl and $C_{3-8}$ cycloalkenyl are preferably substituted with one to three $C_{1-4}$ alkyl, $C_{1-4}$ alkoxy or halo; Q is preferably substituted with one to three $C_{1-4}$ alkyl, $C_{1-4}$ alkoxy, halo, oxo or phenyl; phenyl is preferably substituted with one to three $C_{1-4}$ alkyl, $C_{1-4}$ alkoxy, phenyl, phenoxy, het, halo, —NO$_2$ or —CN.

More preferably, in the meanings of $R_1$, the optional substituents of —(CH$_2$)$_n$-aryl are selected from $C_{1-4}$ alkyl, $C_{1-4}$ alkoxy, phenyl, O-phenyl, het, O-het, halo, —NO$_2$, —CF$_3$, —CN, or —N(C$_{1-4}$ alkyl)$_2$; the optional substituents of —(CH$_2$)$_n$-het are selected from $C_{1-4}$ alkyl, phenyl, phenoxy, het, or halo; in the meanings of $R_2$, the optional substituents of $C_{1-12}$ alkyl are one to three halo, —CN, —NO$_2$, —CF$_3$, —N(R$_3$)$_2$, —SR$_3$, or OH; the optional substituents of $C_{2-12}$ alkenyl and $C_{2-12}$ alkynyl are one to three halo, —CN, NO$_2$, or —CF$_3$; the optional substituents of —(CH$_2$)$_n$-C$_{3-8}$ cycloalkyl and —(CH$_2$)$_n$-C$_{3-8}$ cycloalkenyl are one to three $C_{1-4}$ alkyl, $C_{1-4}$ alkoxy, or halo; the optional substituents of —(CH$_2$)$_n$-aryl are one to three $C_{1-4}$ alkyl, $C_{1-4}$ alkoxy, —CF$_3$—OH, —NO$_2$, —CN, —N(R$_3$)$_2$, —SR$_3$, —SO$_2$(C$_{1-4}$ alkoxy), —(=O)R$_3$, —NHC(=O)R$_3$, one to five halo; the optional substituents of —(CH$_2$)$_n$-het are one to two $C_{1-4}$ alkyl, or halo; the optional substituents of —(CH$_2$)$_n$-Q are one to three $C_{1-4}$ alkyl, $C_{1-4}$ alkoxy, halo, oxo or phenyl; in the meanings of $R_3$ the optional substituents of —(CH$_2$)$_n$-phenyl are one to three $C_{1-4}$ alkyl, $C_{1-4}$ alkoxy, or halo; in the meanings of $R_4$ the optional substituents of —(CH$_2$)$_n$-phenyl are one to three $C_{1-4}$ alkyl, $C_{1-4}$ alkoxy, phenyl, phenoxy, het, halo, —NO$_2$, —CN—; in the meanings of $R_7$ and $R_8$ the optional substituents of —(CH$_2$)$_n$-phenyl are one to three $C_{1-4}$ alkyl, $C_{1-4}$ alkoxy, or halo. In the meanings of $R_2$, the preferred substituent(s), when present, of the —(CH$_2$)$_i$— chain are one or two $C_{1-4}$ alkyl, more preferably one or two methyl groups.

DETAILED DESCRIPTION OF THE INVENTION

For the purpose of the present invention, the carbon content of various hydrocarbon containing moieties is indicated by a prefix designating the minimum and maximum number of carbon atoms in the moiety; i.e., the prefix $C_{ij}$ defines the number of carbon atoms present from the integer "i" to the integer "j", inclusive. Thus, $C_{1-4}$ alkyl refers to alkyl of one to four carbon atoms, inclusive, or methyl, ethyl, propyl, butyl and isomeric forms thereof.

The terms "$C_{1-4}$ alkyl", "$C_{4-8}$ alkyl", "$C_{1-12}$ alkyl", and "$C_{1-18}$ alkyl" refer to an alkyl group having one to four, four to eight, one to twelve, or one to eighteen carbon atoms respectively such as; for example, methyl, ethyl, propyl, butyl, pentyl, hexyl, heptyl, octyl, nonyl, decyl, undecyl, dodecyl, tridecyl, tetradecyl and their isomeric forms thereof, preferably an alkyl group of $R_1$ having four to eight carbon atoms, and an alkyl group of $R_2$ having one to eight carbon atoms.

The terms "$C_{2-12}$ alkenyl" and "$C_{4-8}$ alkenyl" refer to at least one double bond alkenyl group having two to twelve carbon atoms respectively such as; for example, ethenyl, propenyl, butenyl, pentenyl, hexenyl, heptenyl, heptdienyl, octenyl, octadienyl, octatrienyl, nonenyl, undecenyl, dodecenyl, and their isomeric forms thereof, preferably an alkenyl group of $R_1$ having four to eight carbon atoms, and an alkenyl group of $R_2$ having two to eight carbon atoms.

The term "$C_{2-12}$ alkynyl" refers to at least one triple bond alkynyl group having two to twelve carbon atoms such as; for example, ethynyl, propynyl, butynyl, pentynyl, hexynyl, heptynyl, octynyl, octadiynyl, octatriynyl, nonynyl, nonediynyl, and their isomeric forms thereof, preferably an alkynyl group of $R_1$ having four to eight carbon atoms, and an alkenyl group of R having two to eight carbon atoms.

The term "$C_{3-8}$ cycloalkyl" refers to a cycloalkyl having three to eight carbon atoms such as; for example, cyclopropyl, cyclobutyl, cyclopentyl, cyclohexyl, cycloheptyl, cyclooctyl, and their isomeric forms thereof, preferably a cycloalkyl group having five or six carbon atoms.

The term "$C_{3-8}$ cycloalkenyl" refers to a cycloalkenyl having three to six or three to eight carbon atoms such as; for example, cyclopropenyl, cyclobutenyl, cyclopentenyl, cyclohexenyl, cycloheptenyl, cyclooctenyl, and their isomeric forms thereof, preferably a cycloalkyl group having five or six carbon atoms.

The terms "$C_{1-4}$ alkoxy", "$C_{1-6}$ alkoxy", and "$C_{1-8}$ alkoxy" refer to an alkyl group having one to four, one to six, or one to eight carbon atoms respectively attached to an oxygen atom of hydroxyl group such as; for example, methoxy, ethoxy, propyloxy, butyloxy, pentyloxy, hexyloxy, heptyloxy, or octyloxy and their isomeric forms thereof.

The term "aryl" refers to monocarbocyclic or bicarbocyclic aromatic moiety such as; for example phenyl, naphthyl, and biphenyl. Each of these moieties may be substituted as appropriate. Aryl is preferably phenyl or phenyl substituted with $C_{1-4}$ alkyl, $C_{1-4}$ alkoxy, fluoro, chloro, bromo, —$NO_2$, —$CF_3$, —$N(C_{1-4}$ alkyl$)_2$, —$C(=O)R_3$, or —$NC(=O)R_3$.

The term "het" refers to a 5- to 10-membered unsaturated moncyclic or bicyclic heterocyclic moiety having one or more atoms selected from the group consisting of oxygen, nitrogen, and sulfur such as; for example, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyl, 3quinolyl, 1-isoquinolyl, 3-isoquinolyl, 4isoquinolyl, 2-quinazolinyl, 4-quinazolinyl, 2-quinoxalinyl, 1-phthalazinyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 3-isothiazole, 4-isochiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzoisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1-indolyl, 1-indazolyl, 2-isoindolyl, 1-purinyl, 3-isothiazolyl, 4-isothiazolyl and 5-isothiazolyl, preferably pyridyl, quionlinyl, pyrrolyl, thienyl, thiazolyl, or indolyl. Each of these moieties may be substituted with one to two $C_{1-4}$ alkyl, —$NO_2$, fluoro, chloro, or bromo as appropriate.

The term "Q" refers to a 5- to 10-membered saturated monocyclic or bicyclic heterocyclic moiety having one to two atoms selected from the group consisting of oxygen, nitrogen, and sulfur such as, for example, piperidinyl, 2-, 3-, or 4-piperidinyl, [1,4]piperazinyl, 2- or 3-morpholinyl, thiomorpholinyl, dioxolanyl, imidazolidinyl, [1,3]oxathiolanyl, [1,3]oxazolidinyl, pyrrolidinyl, butyrolactonyl, butyrolactamyl, succinimidyl, glutarimidyl, valerolactamyl, 2,5-dioxo-[1,4]-piperazinyl, pyrazolidinyl, 3-oxopyrazolidinyl, 2-oxo-imidazolidinyl, 2,4dioxo-imridazolidinyl, 2-oxo-[1,3]-oxazolidinyl, 2,5-dioxo-[1,3]-oxazolidinyl, isoxazolidinyl, 3-oxo-isoxazolidinyl, [1,3]-thiazolidinyl, 2- or 4-oxo-[1,3]-thiazolidinyl, preferably butyrolactamyl, succinimidyl, glutarimidyl, valerolactamyl, 2,5-dioxo-[1,4]-piperazinyl, 3-oxopyrazolidinyl, 2-oxo-imidazolidinyl, 2,4-dioxo-imidazolidinyl, 2-oxo-[1,3]-oxazolidinyl, 2,5-dioxo-[1,3]-oxazolidinyl, 3-oxo-isoxazolidinyl, 2- or 4-oxo-[1,3]-thiazolidinyl.

The term halo refers to fluoro, chloro, bromo, or iodo, preferably fluoro, chloro, or bromo.

The compounds of the present invention can be converted to their salts, where appropriate, according to conventional methods.

The term "pharmaceutically acceptable salts" refers to acid addition salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate and the like. These salts may be in hydrated form. Some of the compounds of this invention may form metal salts such as sodium, potassium, calcium and magnesium salts and these are embraced by the term "pharmaceutically acceptable salts".

The compounds of formula I of this invention contain a chiral center at the α-position of hydroxamic acids, as such there exist two enantiomers or a racemic mixture of both. This invention relates to both the enantiomers, as well as mixtures containing both the isomers. In addition, depending on the substituents, additional chiral centers and other isomeric forms may be present in any of the $R_2$ groups, and this invention embraces all possible stereoisomers and geometric forms in this group.

$R_1$ is preferably n-butyl, isobutyl, 1-methylpropyl, tert-butyl, n-pentyl, 3-methybutyl, n-hexyl, n-heptyl, n-octyl, phenyl, 4-methylphenyl, 4-ethylphenyl, 4-tert-butylphenyl, 4-isopropylphenyl, 4-chlorophenyl, 4-bromophenyl, 4-fluorophenyl, 4-trifluoromethylphenyl, 4-methoxyphenyl, 4-ethoxyphenyl, 4-n-butyloxyphenyl, benzyl, 4-phenylbenzyl, 2-, 3-, or 4-fluorobenzyl, 2-, 3-, 4-chlorobenzyl, 2-, 3-, 4-bromobenzyl, and 4-ethoxybenzyl. More preferably $R_1$ is n-butyl, n-pentyl, n-hexyl, n-heptyl, n-octyl, phenyl, 4-methylphenyl, 4-ethylphenyl, 4-isopropylphenyl, 4-chlorophenyl, 4-bromophenyl, 4-fluorophenyl, 4-methoxyphenyl, 4-butoxyphenyl, benzyl, 4-fluorobenzyl, 4-chlorobenzyl, 4-bromobenzyl, 4-ethoxybenzyl, 4-phenylphenyl or 4-n-butylphenyl. More preferably $R_1$ is 4-phenylphenyl, 4-n-butylphenyl, 4-fluorophenyl, or 4-methoxyphenyl 4 butoxyphenyl, benzyl, 4-fluorobenzyl, 4-chlorobenzyl, 4-bromobenzyl, 4-ethoxybenzyl, 4-phenylphenyl, 4-n-butylphenyl, biphenyl, 4-chlorobiphenyl, 4-phenoxyphenyl, 4-(pyrid-4-yl)phenyl, and 4-(pyrid-4-yl)oxyphenyl.

R2 is preferably 1-cyano-1-phenyl methyl, 2-cyano ethyl, 2-phenylethyl, 2-bromo-2-phenylethyl, 2-bromoethyl, propyl, isopropyl, 3-chloropropyl, 3-bromopropyl, n-butyl, isobutyl, 3-methylbutyl, 1-methylpropyl, tert-butyl, n-pentyl, 3-methybutyl, n-hexyl, n-heptyl, n-octyl, n-hexadecyl, n-octadecyl, 2-propenyl, 2-propynyl, 3-butenyl, 4-pentenyl, 3-butenynyl, 4-pentenynyl, cyclopentyl, cyclohexyl, cyclohexylmethyl, 2-cyclohexylethyl, 4-cyclohexylbutyl, dimethylaminoethyl, dimethylaminopropyl, diethylaminopropyl, phenylaminomethyl, phenyl, 4-methylphenyl, 4-chlorophenyl, 4-bromophenyl, 4-fluorophenyl, 4-trifluoromethylphenyl, 2-methoxyphenyl, 4-methoxyphenyl, 4-nitrophenyl, 4-ethoxyphenyl, benzyl, 4-methylbenzyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, and 2-methylbenzyl, 3-methylbenzyl, 4-methylbenzyl, 4-ethoxybenzyl, 4-nitrobenzyl, methylcarbonyl, 1-methylcarbonyl, methyl, N-Hydroxy-2-hydroxy-2-[(4-methoxybenzenesultonyl) methyl]-3-(N-(4-methoxybenzenecarbonyl)amino)-propionamide, N-Hydroxy-2-hydroxy-2-(1-methylhydantoin-3-yl)methyl]-3-(4-methoxybenzenesulfonyl)propionamide, N-Hydroxy-2-hydroxy-2-(1,5,5-trimethylhydantoin-3-yl)methyl-3-(4-methoxybenzenesulfonyl)propionamide; N-Hydroxy-2-hydroxy-2-(1-methylhydantoin-3-yl)methyl-3-(4-butoxybenzenesulfonyl)propionamide; N-Hydroxy-2-hydroxy-2-(1-butylhydantoin-3-yl)methyl-3-(4-4 butoxybenzenesulfonyl)propionamide; N-Hydroxy-2-hydroxy-2-(1,5,5-trimethylhydantoin-3-yl)methyl-3-(4-butoxybenzenesalfonyl)propionamide; N-Hydroxy-2-hydroxy-2-(methylthio)methyl-3-(4-butoxybenzenesulfonyl)propionamide; N-Hydroxy-2-hydroxy-2-(phenylthio)methyl-3-(4-butoxybenzenesulfonyl)propionamide; N-Hydroxy-2-hydroxy-2-(benzylthio)methyl-3-(4-butoxybenzenesulfonyl)propionamide; N-Hydroxy-2-hydroxy-2-(pyrid-2-yl)thiomethyl-3-(4-butoxybenzenesulfonyl)propionamide; N-Hydroxy-2-hydroxy-2-(2-methyl-5-oxo-6-hydroxy-2,5-dihydro-1,2,4-triazin-3-yl)thiomethyl-3-(4-butoxybenzenesulfonyl) propionamide; N-Hydroxy-2-hydroxy-2-(2-aminothiazol-5-yl)thiomethyl-3-(4-butoxybenzenesulfonyl)propionamide; N-Hydroxy-2-hydroxy-2-(2-methyl-1,3,4-thiadiazol-5-yl) thiomethyl-3-(4-butoxybenzenesulfonyl)propionamide; N-Hydroxy-2-hydroxy-2-(1-methyl-1H-imidazol-2-yl) thiomeihyl-3-(4-butoxybenzenesulfonyl)propionamide; N-Hydroxy-2-hydroxy-2-(1-methyltetrazol-5-yl) thiomethyl-3-(4-butoxybenzenesulfonyl)propionamide; N-Hydroxy-2-hydroxy-2-(tetrazolo[1,5-b]pyridazin-6-yl) thiomethyl-3-(4-butoxybenzenesulfonyl)propionamide; N-Hydroxy-2-hydroxy-2-(pyrid-2-yl)methylthiomethyl-3-(4-butoxybenzenesulfonyl)propionamide; N-Hydroxy-2-hydroxy-2-(1-methyl-1H-imidazol-2-yl)methylthiomethyl-3-(4-butoxybenzenesulfonyl)propionarnide; N-Hydroxy-2-hydroxy-2-(1-benzyl- I H-imidazol-2-yl)methylthiomethyl-3-(4butoxybenzenesulfonyl)propionamide; N-Hydroxy-2-hydroxy-2-(5-methylisoxazol-3-yl)methylthiomethyl-3-(4-butoxybenzenesulfonyl)propionamide; N-Hydroxy-2-hydroxy-2-(2-benzylthio-2-methylethyl)-3-(4-butoxybenzenesulfonyl)propionamide; N-Hydroxy-2-hydroxy-2-[2-(pyrid-2-yl)thio-2-methyleth yl]-3-(4-butoxybenzenesulfonyl)propionamide; N-Hydroxy-2-hydroxy-2-(1-methylhydantoin-3-yl)methyl-3-(4-chlorobiphenyl-sulfonyl) propionamide; N-Hydroxy-2-hydroxy-2-(1-butylhydantoin-3-yl)methy-3-(4-chlorobiphenylsulfonyl)propionamide; N-Hydroxy-2-hydroxy-2-(1,5,5-trimethylhydantoin-3-yl)methyl-3-(4-chlorobiphenylsulfonyl)propionamide; N-Hydroxy-2-hydroxy-2-(phenylthio)methyl-3-(4-chlorobiphenylsulfonyl)propionamide; N-Hydroxy-2-hydroxy-2-benzylthio)methyl-3-(4-chlorobiphenylsulfonyl) propionamide; N-Hydroxy-2-hydroxy-2-(pyrid-2-yl) methylthiomethyl-3-(4-chlorobiphenylsulfonyl) propionamide; N-Hydroxy-2-hydroxy-2-(5-methylisoxazol-3-yl)methylthiomethyl-3-(4-chlorobiphenylsulfonyl) propionamide; N-Hydroxy-2-hydroxy-2-[2-(1-methylhydantoin-3-yl)methylethyl]-3-(4-chlorobiphenylsulfonyl)propionamide; N-Hydroxy-2-hydroxy-2-[2-(pyril-2-yl)thio-2-methylethyl]-3-(4-chlorobiphenylsulfonyl)propionamide; N-Hydroxy-2-hydroxy-2-(1-methylhydantoin-3-yl)methyl-3-(4-phenoxybenzenesulfonyl)propionamide; N-Hydroxy-2-hydroxy-2-(1-butylhydantoin-3-yl)methyl-3-(4-phenoxybenzenesulfonyl)propionamide; N-Hydroxy-2-hydroxy-2-(1,5,5-trimethylhydantoin-3-yl)methyl-3-(4-phenoxybenzenesulfonyl)propionamide; N-Hydroxy-2-hydroxy-2-(1-benzylhydantoin-3-yl)methyl-3-(4-phenoxybenzenesulfonyl)propionamide; N-Hydroxy-2-hydroxy-2-(phenylthio)methyl-3-(4-phenoxybenzenesulfonyl)propionamide; N-Hydroxy-2-hydroxy-2-(benzylthio)methyl-3-(4-phenoxybenzenesulfonyl)propionamide; N-Hydroxy-2-hydroxy-2-(pyrid-2-yl)methylthiomethyl-3-(4-phenoxybenzenesulfonyl)propionamide; N-Hydroxy-2-hydroxy-2-(1-methyl-1H-imidazol-2-yl)methylthiomethyl-3-(4-phenoxybenzenesulfonyl)propionamide; N-Hydroxy-2-hydroxy-2-[2-(1-methylhydantoin-3-yl)-2-methylethyl-3-(4-phenoxybenzenesulfonyl)propionamide; N-Hydroxy-2-hydroxy-2-[2-(1-methyl-1H-imidazol-2-yl)thio-2-methylethyl]-(4-phenoxybenzenesulfonyl)propionamide; N-Hydroxy-2-hydroxy-2-(1-methylhydantoin-3-yl)methyl-3-[(4-pyrid-4-yl)-benzenesulfonyl)]propionamide; N-Hydroxy-2-hydroxy-2-(1-butylhydantoin-3-yl)methyl-3-[4-(pyrid-4-yl)-benzenesulfonyl]propionamide; N-Hydroxy-2-hydroxy-2-(1,5,5-trimethylhydantoin-3-yl) methyl-3-[4-pyrid-4-yl)benzenesulfonyl]propionamide; N-Hydroxy-2-hydroxy-2-(phenylthio)methyl-3-[4-(pyrid-4-yl)benzenesulfonyl]propionamide; N- Hydroxy-2-hydroxy-2-(benzylthio)methyl -3-[4-(pyrid-4-yl)benzenesulfonyl] propionamide; N-Hydroxy-2-hydroxy-2-(2-benzylthio-2-methylethyl)-3-[4-(pyrid-4-yl)-benzenesulfonyl] propionamide; N-Hydroxy-2-hydroxy-2-(1,5,5-trimethylhydantoin-3-yl)methyl-3-[4-pyrid-4-yl) oxybenzenesulfonyl]propionamide or N-Hydroxy-2-hydroxy-2-(benzylthio)methyl-3-[4-(pyrid-4-yl) oxybenzenesulfonyi]pripionamide. 2-phenylcarbonyl ethyl, isopropylcarbonyl, methoxycarbonyl, ethoxycarbonyl, 1,1-ethoxycarbonyl methyl, 2,2-ethoxycarbonyl ethyl, 1,2-ethoxycarbonyl ethyl, 2-methoxycarbonyl propyl, 3-methoxycarbonyl propyl, 1-ethoxycarbonyl methyl, 1-ethoxycarbonyl ethyl, phenylcarbonyl, phenylcarbonyl methyl, pyridylcarbonyl methyl, pyridylmethyl, pyridylethyl, quionlinylmethyl, pyrrolyl methyl, indolyl methyl, thienyl, thiazolyl, thienylmethyl, thienylethyl, piperdinyl methyl, piperazinyl methyl, morpholino methyl, morpholino ethyl, morpholino propyl, thiomorpholino methyl, thiomorpholino propyl, 4-methoxybenzenesulfonyl methyl, 3-(4-methoxybenzenesulfonyl)amino propyl, 3-(4-methoxybenzenesulfonyl)propyl, 3-hydroxy, amino, 3-phenoxy propyl, 2-phenyl ethyloxy, (4-butoxybenzenesulfonyl) methyl, methyl-3-(1,5,5-trimethylhydantoin), methyl-3-(1-butyl-5,5- dimethylhydantoin), (4-methoxybenzenesulfonyl)methyl, (4-chlorobenzenesulfonyl)-methyl, (4-bromobenzenesulfonyl)methyl, (n-butylsulfonyl)methyl, (n-octylsulfonyl)-methyl, 3-(4-methoxybenzenesulfonyl) propyl, (4-methylbenzenesulfonyl)methyl, (benzenesulfonyl)methyl, (4-phenylbenzenesulfonyl) methyl, (4-n-butylphenylsulfonyl)methyl, methyl-3-(1-methylhydantoin), methyl-3-(1-butylhydantoin), methyl-3-(5,5-dimethylhydantoin), benzenecarbonylamino or cyclopentanylcarbonylamino. More preferably $R_2$ is (4-methoxybenzenesulfonyl)-methyl, (4-fluorobenzenesulfonyl)methyl, (4-phenylbenzenesulfonyl)methyl, (4-n-butylphenylsulfonyl)methyl, benzenecarbonylamino or cyclopentanylcarbonylamino piperazinyl-methyl,4-(methanesulfonyl)piperazinylmethyl, morpholinomethyl, (1-methylhydantoin-3-yl)methyl,(1,5,5-trimethylhydantoin-3-yl)methyl, (1-butylhylhydantoin-3-yl)methyl, 2-(1-methyl-hydantoin-3-yl)methyl-3-methylethyl, phenylthiomethyl, (2-methoxy)phenylthiomethyl, benzylthiomethyl, (pyrid-2-yl)thiomethyl, (pyrid-2-yl)methylthiomethyl, (5-methylisoxazol-3-yl)thiomethyl, (5-methylisoxazol-3-yl)methylthiomethyl, 2-benzylthio-2-methylethyl, 2-(pyrid-2-yl)methylthio-2-methyl-ethyl, 2-(1-methyl-1H-imidazol-2-yl)methylthio-3-methylethyl, 2-(1-benzyl-1H-imidazol-2-yl)methylthio-2-methylethyl, and 2-(5-methylisoxazol-3-yl)methylthio-2-methylethyl Y is preferably a hydroxy group.

Examples of the compounds of this invention are as follows:
a. N-Hydroxy-2-hydroxy-2-[(4-methoxybenzenesulfonyl) methyl]-3-(4-phenylbenzenesulfonyl)-propionamide,
b. N-Hydroxy-2-hydroxy-2-[(4-methoxybenzenesulfonyl) methyl]-3-(4-fluorobenzenesulfonyl)-propionamide,
C. N-Hydroxy-2-hydroxy-2-[(4-methoxybenzenesulfonyl) methyl]-3-(4-n-butylbenzenesulfonyl)-propionamide,
d. N-Hydroxy-2-hydroxy-2-[(4-methoxybenzenesulfonyl) methyl]-3-(4-methoxybenzenesulfonyl)-propionamide,
e. N-Hydroxy-2-hydroxy-2-[(4-methoxybenzenesulfonyl) methyl]-3-(N-benzenecarbonylamino)-propionamide,
f. N-Hydroxy-2-hydroxy-2-[(4-methoxybenzenesulfonyl) methyl]-3-[N-(cyclopentylcarbonyl)amino]-propionamide, or
g. N-Hydroxy-2-hydroxy-2-[(4-methoxybenzenesulfonyl) methyl]-3-(N-(4-methoxybenzenecarbonyl)amino)-propionamide.

The compounds of this invention can be prepared in accordance to the process discussed below.

In Scheme I, $R_1$ and $R_2$ are the groups as defmed previously. Substituted malonate esters 2 are either obtained commercially, or can be readily prepared from structure 1 by methods well known to those skilled in the art. For example, reaction of an enolate of structure 1, generated by an appropriate base in an appropriate solvent, with an alkylating agent $R_2$-I (I is bromo, chloro, tosylate, mesylate, epoxides, etc.) provides the desired substituted malonate esters 2. See: *Organic Synthesis*, Vol. 1, p 50 (1954); *Organic Synthesis*, Vol. 3, p 495 (1955). Compound 2 is hydrolyzed to mono-acid compound 3 by reaction with one equivalent of an appropriate base such as alkali hydroxide in an appropriate solvent at a temperature ranging from 0° C. to 30° C. In the presence of formaldehyde and piperidine in an appropriate solvent such as pyridine, ethanol, dioxane at refluxing temperatures, compound 3 is converted to acrylic esters 4. In many cases, acrylic esters 4 are commercially available. Acrylic esters 4 may be converted to glycidic esters 5 by oxidation with meta-chloroperoxybenzoic acid (MCPBA) in refluxing ethylene dichloride in the presence of a radical inhibitor such as 4,4'-thiobis-(6-t-butyl-3-methyl-phenol). See: *J.C.S.Chem.Comm.*, pp 64–65 (1972). A thiol (H-SR$_1$) is added to the glycidic ester 5 at room temperature to afford sulfide esters 6 in the presence of a base such as sodium hydride in dry THF, or potassium carbonate in toluene, or a tertiary amine in chloroform. The resultant sulfides 6 are readily oxidized to sulfones 7 by an oxidizing agent such as MCPBA in an appropriate solvent such as methylene chloride, or using hydrogen peroxide in acetic acid as solvent. Alternatively, glycidic esters 5 may be converted to sulfones 7 directly by reaction with sodium sulfinate salts in solvents such as DMF or toluene. The esters can be hydrolyzed by procedures well known in the art such as using 6N HCl and refluxing for 10 to 20 hours or using iodotrimethylsilane in chloroform, or by saponification with aqueous alkali in alcoholic solvents at 0° C. to room temperature, to afford free acids 8. Coupling of acids 8 with hydroxylamine hydrochloride to form hydroxamates 10 may be achieved by several routes well known to those skilled in the art. For example, acids 8 can be activated by chloroethylformate in dry THF or a similar compatible solvent, or by a carbodiimide condensing agent such as EDC, with or without HOBT, in DMF and methylene chloride. A tertiary amine is required in both situations. The subsequent reaction of activated 8 with hydroxylamine provides the desired hydroxamic acid derivatives. Alternatively, acids 8 may be condensed, using the same reagents as described above, or using two equivalents of EDC in aqueous THF, with benzyl-protected hydroxylamine hydrochloride, to produce the protected hydroxamates 9. Compounds 9 are often easier to purify, and may readily be hydrogenolytically cleaved to the free hydroxamates 10 by a palladium catalyst in alcoholic solvents. Other protected hydroxylamines, such as tert-butyl hydroxylamine may also be used, and the free hydroxamric acid can be obtained by treating it with trifluoroacetic acid.

A second method of preparing the compounds of the invention particularly applicable to compounds of formula I wherein the $R_2$ group contains heteroatoms is to utilize commercially available bromomethyl acrylic acid esters such as 11, as shown in Scheme II. Treatment of 11 with thiols affords compounds 12. The reaction may be accomplished in dioxane, ethanol, toluene, or other appropriate solvent, at room temperature or reflux, with a base such as sodium bicarbonate or piperidine. See: *Annelen*, Vol. 564, pp 73–78 (1949). Ester 11 may also be converted directly to the sulfone 13 by treatment with sodium suffinate salts in DMF, toluene, methanol, or other appropriate solvent at room temperature or reflux, with or without sodium iodide as catalyst. See: *Tetrahedron Lett.*, Vol. 28, pp 813–816 (1987). Sulfides 12 or sulfones 13 can be oxidized to glycidic esters 14 by oxidation with a sufficient amount of MCPBA in refluxing ethylene dichloride in the presence of a radical inhibitor such as 4,4'-thiobis-(6-t-butyl-3-methyl-phenol), as referenced above. The glycidic esters 14 may be reacted with nucleophilic compounds W—H or alkaline salts thereof (wherein W is a group attached via a heteroatom such as oxygen, nitrogen, sulfuir, or halogen) to afford the α-hydroxy esters 7 ($R_2$=CH$_2$—W). These reactions may be accomplished in methanol, DMF, toluene, or other appropriate solvents at room temperature or reflux. See: *Tetrahedron*, Vol. 51, pp 11841–11854 (1995) for an example of this reaction. Nucleophilic addition to glycidic esters may be facilitated by coordinating ions such as Mg$^{2+}$or other species such as titanium alkoxides. See: *Tetrahedron Lett.*, Vol. 28, pp 4435–4436 (1987) and *J. Org. Chem.*, Vol. 50, pp 1560–1563 (1985). Comrpounds 7 may be converted to hydroxamic acids 10 according to the methods described in Scheme I. Alternatively, bromomethyl acrylic acid esters 11 may be reacted first with nucleophiles W—H or alkaline salts thereof under the above-described conditions to afford acrylic esters 4, wherein $R_2$ is —$CH_2W$. Compounds 4 can be converted to hydroxamic acids 10, wherein $R_2$ is —$CH_2W$, according to the procedures described for Scheme I.

Scheme III illustrates the special case of Scheme II wherein glycidic ester 14 is reacted with a thiol or thiolate, as the nucleophile W—H or its alkaline salt, to afford the α-hydroxy esters 7 ($R_2$=—$CH_2$—S—$R_4$). The reaction may be accomplished in THF, toluene, or other appropriate solvent, with the thiol and an appropriate base such as sodium hydride or potassium carbonate, at room temperature or reflux. These esters may be oxidized to the bis-sulfone esters 15 with MCPBA in methylene chloride, or hydrogen peroxide in acetic acid. Alternatively, the bis-sulfone esters 15 may be prepared directly from glycidic esters 14 by reaction with the sodium sulfinate salts in DMF, toluene, methanol, or other appropriate solvent at room temperature or reflux, with or without sodium iodide as catalyst. Hydrolysis of bis-sulfone esters 15 to the carboxylic acids 8 ($R_2$=—$CH_2$—$S(O)_2$—$R_4$), and subsequent conversion to hydroxamic acids 10 ($R_2$=—$CH_2$—$S(O)_2$—$R_4$), may be accomplished in accordance with the methods described in Scheme 1. In the special case wherein $R_1$ is the same as $R_4$, the resulting hydroxamic acids are achiral molecules.

Another variation of Scheme II is shown in Scheme IV, wherein glycidic ester is reacted with a nitrile compound $R_3CN$ in the presence of an acidic catalyst, preferably boron trifluoride etherate in methylene chloride, to afford the oxazoline esters 16. See: *Recueil des Travaux Chimiques des Pays-Bas*, Vol. 111, pp 69–74 (1992). The reaction is accomplished in several days at room temperature. The oxazoline esters 16 are hydrolyzed to the α-hydroxy esters 7 ($R_2$=—$CH_2$—$NHCOR_3$) in the presence of acids, preferably oxalic acid in refluxing ethanol. Subsequent conversion of the esters 7 to the hydroxamic acids 10 ($R_2$ =—$CH_2$—$NHCOR_3$) is accomplished by the methods described in Scheme I.

Scheme V illustrates a method whereby compounds of this invention having a heterocyclic moiety may be prepared. Glycidic esters 14 may be reacted with t-butoxycarbonyl (Boc)-protected aminoacrylonitrile, for example, according to the methods of Scheme IV, to afford initially the oxazoline esters 17, and then the α-hydroxy esters 18 ($R_2$=—$CH_2$—$NHCOCH_2NHBoc$). Deprotection of the Boc group with trifluoroacetic acid, followed by reaction of the amine with an acylating agent such as ethyl chloroformate in a solvent such as methylene chloride in the presence of a tertiary amine base such as triethylamine, and subsequent intramolecular acylation of the amide nitrogen may be utilized to afford compounds 19, containing, for example, a hydantoin ring. Conversion of compounds 19 to hydroxamic acids 20 may be accomplished by the methods described in Scheme I. By similar reactions well known in the art, and utilizing other readily available nitrile derivatives and acylating or alkylating agents, compounds 19 containing other nitrogen heterocycles can be prepared, and converted to compounds of this invention.

Scheme VI describes a method of preparing compounds of formula I, wherein Y=—$NH_2$ or —$NHR_9$, via the glycidic esters 5. Thus reaction of glycidic esters 5 with sodium azide in aqueous ethanol affords the azido alcohols 21. Refluxing the azido alcohols with triphenylphosphine in acetonitrile generates the aziridines 22. The aziridines undergo ring opening with thiol $HSR_1$ (followed by oxidation to the sulfone with MCPBA) or with sulfinate salts directly to afford the α-amino esters 23. This reaction may be aided by using boron trifluoride etherate as a Lewis acid catalyst, in methylene chloride. See: *J. Org. Chem.*, Vol. 60, p 790 (1995). Compounds 23 may be converted to the amino acids 24, and thence to hydroxamates 25 by the methods described in Scheme I. The amino group of compounds 22, 23, 24, or 25 may be protected by a Boc group or other amino-protecting group by methods well known to those skilled in the art.

The preparation of compounds of formula I wherein Y=F can be accomplished by the methods shown in Scheme VII. The α-hydroxy esters 7 may be converted to the a-fluoro esters 26 by use of diethylaminosulfur trifluoride (DAST) in a solvent such as methylene chloride at 0° C. to room temperature. See: *J. Org. Chem.*, Vol. 40, p 574 (1975). Compounds 26 may be converted to the α-fluoro hydroxamic acids 27 by the methods described in Scheme I.

The chemistry in Schemes I–VII proceeds through achiral or racemic intermediates and pure enantiomers of the final products may be obtained by resolution of intermediates 5–9, 14–19, 21–24, or 26 or final products 10, 20, 25, or 27 by chiral chromatography or by classical derivatization methods such as chiral salt formation of carboxylic acid intermediates such as 8 or 24.

The present invention also provides novel compounds of formula 8

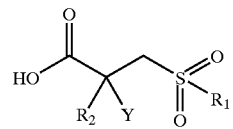

8 or pharmaceutical acceptable salts thereof wherein $R_1$, $R_2$ and Y are as defined above. Examples of the compounds of formula 8 are as follows:

2-Hydroxy-2-(1-butylhydantoin-3-yl)methyl-3-(4-butoxybenzenesulfonyl)propionic acid;

2-Hydroxy-2-(1,5,5-trimethylhydantoin-3-yl)methyl-3-(4-butoxybenzenesulfonyl)propionic acid;

2-Hydroxy-2-(phenylthio)methyl-3-(4-butoxybenzenesulfonyl)propionic acid;

2-Hydroxy-2-(benzylthio)methyl-3-(4-butoxybenzenesulfonyl)propionic acid;

2-Hydroxy-2-(2-benzylthio-2-methylethyl)-3-(4-butoxybenzenesulfonyl)propionic acid;

2-Hydroxy-2-(1-methylhydantoin-3-yl)methyl-3-(4-chloro-biphenylsulfonyl)propionic acid;

2-Hydroxy-2-(1-butylhydantoin-3-yl)methyl-3-(4-chloro-biphenylsulfonyl)propionic acid;

2-Hydroxy-2-(1,5,5-trimethylhydantoin-3-yl)methyl-3-(4-chlorobiphenylsulfonyl)propionic acid;

2-Hydroxy-2-(phenylthio)methyl-3-(4-chlorobiphenyl-sulfonyl)propionic acid;

2-Hydroxy-2-(benzylthio)methyl-3-(4-chlorobiphenyl-sulfonyl)propionic acid;

2-Hydroxy-2-(pyrid-2-yl)thiomethyl-3-(4-chlorobiphenyl-sulfonyl)propionic acid;

2-Hydroxy-2-(5-methylisoxazol-3-yl)methylthiomethyl-3-(4-chlorobiphenylsulfonyl)propionic acid;

2-Hydroxy-2-[2-(1-methylhydantoin-3-yl)-2-methylethyl]-3-(4-chlorobiphenylsulfonyl)propionic acid;

2-Hydroxy-2-(2-benzylthio-2-methylethyl)-3-(4-chloro-biphenylsulfonyl)propionic acid;

2-Hydroxy-2-(1-methylhydantoin-3-yl)methyl-3-(4-phenoxy-benzenesulfonyl)propionic acid;

2-Hydroxy-2-(1-butylhydantoin-3-yl)methyl-3-(4-phenoxy-benzenesulfonyl)propionic acid;

2-Hydroxy-2-(1,5,5-trimethylhydantoin-3-yl)methyl-3-(4-phenoxybenzenesulfonyl)propionic acid;

2-Hydroxy-2-(phenylthio)methyl-3-(4-phenoxybenzene-sulfonyl)propionic acid;

2-Hydroxy-2-(benzylthio)methyl-3-(4-phenoxybenzene-sulfonyl)propionic acid;

2-Hydroxy-2-[2-(1-methylhydantoin-3-yl)-2-methylethyl]-3-(4-phenoxybenzenesulfonyl)propionic acid;

2-Hydroxy-2-[2-(1-methyl-1H-imidazol-2-yl)thio-2-methyl-ethyl]-(4-phenoxybenzenesulfonyl)propionic acid;

2-Hydroxy-2-(1,5,5-trimethylhydantoin-3-yl)methyl-3-[4-(pyrid-4-yl)benzenesulfonyl]propionic acid;

2-Hydroxy-2-(phenylthio)methyl-3-[4-(pyrid-4-yl)benzene-sulfonyl]propionic acid;

2-Hydroxy-2-(1,5,5-trimethylhydantoin-3-yl)methyl-3-[4-(pyrid-4-yl)oxybenzenesulfonyl]propionic acid.

The pharmaceutical compositions of this invention may be prepared by combining the compounds of formula I of this invention with a solid or liquid pharmaceutically acceptable carrier, and optionally, with pharmaceutically acceptable adjuvants and excipients employing standard and conventional techniques. Solid form compositions include powders, tablets, dispersible granules, capsules and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water, water-propylene glycol, and water-polyethylene glycol systems, optionally containing conventional coloring agents, flavoring agents, stabilizers and thickening agents.

The pharmaceutical composition is provided by employing conventional techniques. Preferably the composition is in unit dosage form containing an effective amount of the active component, that is, the compounds of formula I according to this invention.

The quantity of active component, that is the compounds of formula I according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

In therapeutic use for treating a patient, suffering from or susceptible to diseases involving connective tissue degradation, or inhibiting various enzymes from the matrix metalloproteinase family, including collagenase, stromelysin, and gelatinase, the compounds or pharmaceutical compositions thereof will be administered orally, parenterally and/or topically at a dosage to obtain and maintain a concentration, that is, an amount, or blood-level of active component in the patient undergoing treatment which will be effective to inhibit such enzymes. Generally, an effective amount of the active compound will be in the range of about 0.1 to about 100 mg/kg. It is to be understood that the dosages may vary depending upon the requirements of the patient, the severity of connective tissue degradation being treated, and the particular compounds being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of the present invention inhibit various enzymes from the matrix metalloproteinase family, predominantly stromelysin and gelatinase, and hence are useful for the treatment of matrix metallo endoproteinase diseases such as osteoarthritis, rheumatoid arthritis, septic arthritis, osteopenias such as osteoporosis, tumor metastasis (invasion and growth), periodontitis, gingivitis, corneal ulceration, dermal ulceration, gastric ulceration, inflammation, asthma and other diseases related to connective tissue degradation. Such diseases and conditions are well known and readily diagnosed by physician of ordinary skill.

Pharmaceutical compositions for parenteral administration will generally contain a pharmaceutically acceptable amount of the compounds according to formula I as a soluble salt (acid addition salt or base salt) dissolved in a pharmaceutically acceptable liquid carrier such as; for example, water-for-irection and a suitably buffered isotonic solution having a pH of about 3.5–6. Suitable buffering agents include; for example, trisodium orthophosphate, sodium bicarbonate, sodium citrate, N-methylglucamine, L(+)-lysine and L(+)-arginine, to name a few. The compounds according to formula I generally will be dissolved in the carrier in an amount sufficient to provide a pharmaceutically acceptable injectable concentration in the range of about 1 mg/ml to about 400 mg/ml. The resulting liquid pharmaceutical composition will be administered so as to obtain the above-mentioned inhibitory effective amount of dosage. The compounds of formula I according to this invention are advantageously administered orally in solid and liquid dosage forms.

The compounds and their preparations of the present invention will be better understood in connection with the following examples, which are intended as an illustration of and not a limitation upon the scope of the invention.

EXAMPLE 1

Preparation of N-Hydroxy-2-hydroxy-2-[(4-methoxybenzenesulfonyl) methyl]-3-(4-phenylbenzenesulfonyl)-propionamide

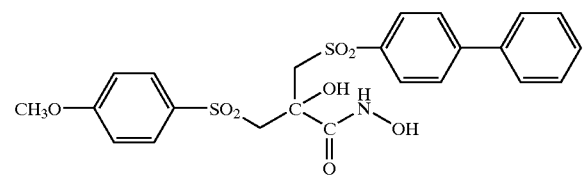

Step 1 Preparation of 2-[(4-Methoxybenzenethio)methyl]-acrylic Acid, Ethyl Ester.

To a mixture of ethyl bromomethylacrylate (1.6 g, 8.3 mmol) and 1.0 mL (8.1 mmol) of 4-methoxythiophenol in ethanol, cooled in an ice-water bath, is added, dropwise and with stirring, 8 mL of a 1M aqueous solution of sodium bicarbonate. The reaction mixture is allowed to warm to ambient temperature, and stirred for 6 hours. The mixture is then concentrated, taken up in ethyl acetate, and washed twice with aqueous 10% hydrochloric acid and once with brine. It is dried over sodium sulfate and evaporated in vacuo to a pale yellow oil. Chromatography on silica gel, eluting with methylene chloride, affords the title compound as a colorless oil.

$^1$H NMR (CDCl$_3$) δ 7.33, 6.82, 6.07, 5.32, 4.23, 3.78, 3.63, 1.31.

Step 2 Preparation of 2-(4-Methoxybenzenesulfonyl) methyl-oxiranecarboxylic Acid, Ethyl Ester.

To 2[(4-methoxybenzenesulfonyl)methyl]-acrylic acid, ethyl ester (38.4 g, 0.152 mol) in 200 mL of ethylene dichloride is added a small amount of the radical inhibitor 4,4'-thiobis-(6-t-butyl-3-methylphenol) [Ref: *J.C.S. Chem. Commun.*, 1972, pp 64–65]. Technical grade m-chloroperoxybenzoic acid (MCPBA, 154 g) is added portionwise over about 45 minutes. The reaction becomes a heavy white slurry. Additional ethylene dichloride (150 mL) is introduced to facilitate stirring. The reaction is refluxed overnight, then cooled and concentrated under reduced pressure. The residue is mixed with ethyl acetate (250 mL) and aqueous sodium sulfite. Solid potassium bicarbonate is then slowly added. The phases are separated , and the aqueous phase is extracted with additional ethyl acetate (100 mL). The combined organic phases are washed with several portions of aqueous potassium bicarbonate, then saturated brine, and finally dried over magnesium sulfate. Filtration and evaporation provides the crude product as a pale yellow oil. Chromatography on silica gel, eluting with a gradient of 40% to 60% ethyl acetate in hexanes, affords the title compound. m.p. 77–79° C.;

$^1$H NMR (DMSO-d$_6$) δ 7.78, 7.16, 4.11, 4.04, 3.85, 3.73, 2.95, 1.16. $^{13}$C NMR (DMSO-d$_6$) δ 168.4, 164.3, 132.3, 131.0, 115.3, 62.5, 58.5, 56.6, 53.2, 51.6, 14.6.

Step 3 Preparation of 2-Hydroxy-2-[(4-methoxybenzenesulfonyl)methyl]-3-(4-phenylbenzenethio)-propionic Acid, Ethyl Ester.

Sodium hydride (0.212 g, 60% in oil) is placed in a flask and washed with hexane. The hexane is decanted. Biphenyl mercaptan (0.82 g, 5.3 mmol) is added as a solution in dry tetrahydrofaran (25 mL). There is foaming, and a heterogeneous mixture results. The reaction is stirred for 5 minutes at ambient temperature, and then a solution of 2-(4-methoxybenzenesulfonyl)methyl-oxiranecarboxylic acid, ethyl ester (1.46 6, 4.9 mmol) in 25 mL of dry tetrahydrofuran is added. The mixture, which turns yellow, is stirred overnight at ambient temperature. The reaction is quenched with 1N HCl and tetrahydrofuran is removed under reduced pressure. The product is extracted with ethyl acetate. The organic phase is dried over magnesium sulfate, filtered, concentrated, and chromatographed on silica gel to afford the title compound as a white solid.

$^1$H NMR (CDCl$_3$) δ 7.81, 7.6–7.35, 6.98, 4.11, 3.98, 3.87, 3.68, 3.28, 1.21.

Step 4 Preparation of 2-Hydroxy-2-[(4-methoxybenzenesulfonyl)methyl]-3-(4-phenylbenzenesulfonyl)-propionic Acid, Ethyl Ester.

To a solution of 2-hydroxy-2-[(4-methoxybenzenesulfonyl)methyl]-4-phenylbenzenethio)-propionic acid, ethyl ester (0.99 g, 2 mmol) in 100 mL of methylene chloride is added solid MCPBA (1.3 g, 68% by weight). The reaction mixture is stirred overnight at ambient temperature. Methylene chloride is removed under reduced pressure, and the residue is partitioned between ethyl acetate and aqueous sodium sulfite. The organic phase is washed with several portions of aqueous potassium bicarbonate to remove m-chlorobenzoic acid. It is then washed with brine, dried over magnesium sulfate, filtered, and concentrated to afford the title compound as a white solid.

$^1$H NMR (CDCl$_3$) δ 7.92, 7.80–7.72, 7.6, 7.47, 6.97, 4.29, 3.97, 3.86–3.58, 1.36.

Step 5 Preparation of 2-Hydroxy-2-[(4-methoxybenzenesulfonyl)methyl]-3-(4-phenylbenzenesulfonyl)-propionic Acid.

To a solution of 2-hydroxy-2-[(4-methoxybenzenesulfonyl)methyl]-3-(4-phenylbenzenesulfonyl)propionic acid, ethyl ester (0.70 g, 1.3 mmol) in 25 mL of methanol is added sodium hydroxide (25 mmol in 10 mL of water). The reaction mixture is stirred at ambient temperature for 1 hour, and then quenched by the addition of 25 mL of 1N HCl. Methanol is removed under reduced pressure, and the product is extracted with several portions of ethyl acetate. The organic phase is washed with brine, dried over magnesium sulfate, filtered, and concentrated to afford the title compound as a white solid.

$^1$H NMR (CDCl$_3$) δ 7.95, 7.82–7.72, 7.61–7.46, 6.98, 3.86, 3.86–3.70.

Step 6 Preparation of N-Benzyloxy-2-hydroxy-2-[(4-methoxybenzenesulfonyl) methyl]-3-(4-phenylbenzenesulfonyl)-propionamide.

To 2-hydroxy-2-[(4-methoxybenzenesulfonyl)methyl]-3-(4-phenylbenzenesulfonyl)propionic acid (0.6 g, 1.2 mmol) in 50 mL of methylene chloride is added 1-hydroxybenzotriazole monohydrate (0.185 g, 1.36 mmol), O-benzylhydroxylamine hydrochloride (0.218 g, 1.36 nmol), diisopropylethylamine (0.177 g, 1.36 mmol), and 1-(3-dimethylaminopropyl)-3-ethylcarbodiimide hydrochloride (EDC, 0.262 g, 1.36 mmol), in that order. The clear, colorless solution is stirred overnight at ambient temperature. Methylene chloride is removed under reduced pressure and the residue is partitioned between ethyl acetate and water. The organic phase is washed with several portions of 1N HCl and then with aqueous potassium bicarbonate. It is dried over magnesium sulfate, filtered, concentrated, and chromatographed on silica gel. Elution with 1:1 ethyl acetate:hexanes affords the title compound as a white solid.

$^1$H NMR (CDCl$_3$) δ 7.95, 7.83–7.74, 7.5–7.25, 7.01, 4.99, 3.88, 4.0–3.6.

Step 7 Preparation of N-Hydroxy-2-hydroxy-2-[(4-methoxybenzenesulfonyl) methyl]-3-(4-phenylbenzenesulfonyl)-propionamide.

A mixture of N-benzyloxy-2-hydroxy-2-[(4-methoxybenzenesulfonyl)methyl]-3-(4-phenylbenzenesulfonyl)-propionamide (0.152 g), 10% palladium on carbon, and 50 mL of absolute ethanol is placed under 20 psi of hydrogen, and agitated overnight at ambient temperature. The mixture is filtered through a Celite pad, rinsing with ethanol and with ethyl acetate. Concentration of the filtrate affords the title compound.

m.p. 72–76° C. (softening), 120–125° C. (decomposition with bubbling); $^1$H NMR (DMSO-d$_6$) δ 7.9–7.6, 7.55–7.40, 7.1–7.0, 3.82, 3.9–3.7.

Step 8 Racemic N-Hydroxy-2-hydroxy-2-[(4-methoxybenzenesulfonyl)methyl]-3-(4-phenylbenzenesulfonyl)-propionamide is resolved by chiral chromatography to yield enantiomer A and enantiomer B.

Chiral chromatography is performed on a preparative Chiralpak AD column 5.0×50 cm, eluting with methanol at 70 mL/min. The two samples resulting from this chromatography are separately dissolved in methanol, stirred with activated charcoal, filtered through celite and evaporated to dryness to yield purified Enantiomer A and Enantiomer B.

EXAMPLE 2

Preparation of N-Hydroxy-2-hydroxy-2-[(4-methoxybenzenesulfonyl) methyl]-3-(4-fluorobenzenesulfonyl)-propionamide

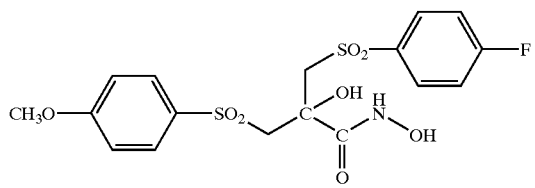

Following the general procedure outlined in EXAMPLE 1 (steps 1 to 7) and making non-critical variations, but starting with p-fluorophenyl mercaptan in step 3, in place of biphenyl mercaptan, the title compound is obtained.

m.p. 85–90° C. (softening), 110–115° C. (decomposition with bubbling); $^1$H NMR (DMSO-$d_6$) $\delta$ 10.6, 8.86, 7.92–7.87, 7.75–7.72, 7.46–7.40, 7.11–7.08, 5.64, 3.85–3.69.

EXAMPLE 3

Preparation of N-Hydroxy-2-hydroxy-2-[(4-methoxybenzenesulfonyl) methyl]-3-(4-n-butylbenzenesulfonyl)-propionamide

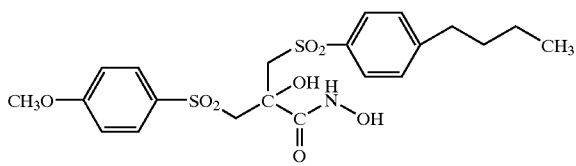

Following the general procedure outlined in EXAMPLE 1 (steps 1 to 7) and making non-critical variations, but starting with p-n-butylphenyl mercaptan in step 3, in place of biphenyl mercaptan, the title compound is obtained.

m.p. 63–68° C. (softening), 150–160° C. (decomposition with bubbling); $^1$H NMR (DMSO-$d_6$) $\delta$ 10.6, 7.76–7.71, 7.43–7.40, 7.11–7.08, 5.6, 3.75–3.72, 2.70–2.65, 1.60–1.55, 1.35–1.27, 0.93–0.88.

EXAMPLE 4

Preparation of N-Hydroxy-2-hydroxy-2-[(4-methoxybenzenesulfonyl)methyl]-3-methoxybenzenesulfonyl)propionamide

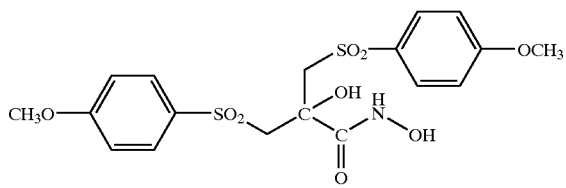

Following the general procedure outlined in EXAMPLE 1 (steps 1 to 7) and making non-critical variations, but starting with p-methoxyphenyl mercaptan in step 3, in place of biphenyl mercaptan, the title compound is obtained as a white solid.

m.p. 75–80° C. (softening), 150–165° C. (decomposition with bubbling); $^1$H NMR (DMSO-$d_6$) $\delta$ 10.55, 8.83, 7.71, 7.08, 5.53, 3.83, 3.69; $^{13}$C NMR (DMSO-$d_6$) $\delta$ 166.6, 163.5, 133.1, 130.7, 114.7, 73.5, 62.0, 56.2; IR (mull) cm$^{-1}$ 3417, 3342, 3316, 3102, 3077, 1682, 1597, 1581, 1520, 1498, 1324, 1295, 1271, 1257, 1150, 1089, 1074; Calculated for $C_{18}H_{21}NO_9S_2$: C, 47.05; H, 4.61; N, 3.05; Found: C, 47.01; H, 4.56; 3.07.

EXAMPLE 5

Preparation of N-hydroxy-2-hydroxy-2-[(4-methoxybenzenesulfonyl) methyl]-3N-benzenecarbonylamino)-propionamide

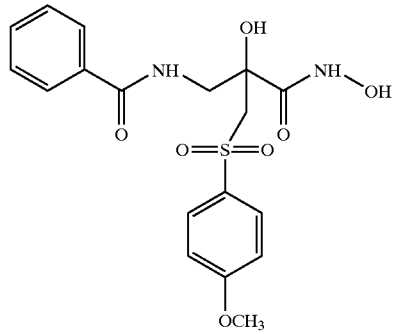

Step 1 Preparation of 2-Hydroxy-2-[(4-methoxybenzenesulfonyl)methyl]-3-(N-benzenecarbonylamino)-propionic Acid, Ethyl Ester.

2-Methoxybenzenesulfonyl)methyl-oxiranecarboxylic acid, ethyl ester (from EXAMPLE 1, Step 2, 0.3 g, 1 mmol), boron trifluoride etherate (0.495 mL, 4.0 mmol), and benzonitrile (0.36 mL, 4.0 mmol) are dissolved in 40 mL of methylene chloride. The reaction mixture is stirred at ambient temperature under a nitrogen atmosphere for three days, with the addition two times of 0.50 mL of boron trifluoride etherate. The solvent is removed under reduced pressure. The residue is dissolved in ethyl acetate and washed with saturated sodium bicarbonate and with brine, and dried over magnesium sulfate. The crude product is dissolved in 40 mL of absolute ethanol. Oxalic acid (0.30 g, 3.3 mmol) is added, and the solution is heated to 65° C. for 19 hours. The solvent is removed under reduced pressure. The oily residue is dissolved in ethyl acetate and washed with saturated sodium bicarbonate and with brine, and dried over magnesium sulfate. Chromatography on silica gel, eluting with 1:1 ethyl acetate:hexanes affords the title compound as a white solid. $^1$H NMR (CDCl$_3$) $\delta$ 7.82–7.71, 7.55–7.41, 7.02–6.99, 6.57, 4.29–4.17, 3.88, 3.85–3.72, 3.60–3.56, 1.32–1.28; MS (ES+) 422.1 (M+H), (ES−) 420.1 (M−H).

Step 2 Preparation of 2-hydroxy-2-[(4-methoxybenzenesulfonyl)methyl]-3-(N-benzenecarbonylamino)-propionic acid.

A solution of 2-hydroxy-2-[(4-methoxybenzenesulfonyl)methyl]-3-(N-benzenecarbonylamino)-propionic acid, ethyl ester (0.27 g) in 4 mL of methanol is stirred with 1 mL of 1N sodium hydroxide for 3 hours. The reaction mixture is acidified with 1N HCl and the solvent is removed under reduced pressure. The residue is triturated twice with warm ethyl acetate. The ethyl acetate is removed, affording the title compound as a white solid.

$^1$H NMR (MeOD) $\delta$ 7.86–7.76, 7.54–7.39, 7.06–7.03, 3.91–3.85, 3.77–3.62; MS (ES+) 394.1 (M+H), (ES−) 392.1 (M−H).

Step 3 Preparation of N-Hydroxy-2-hydroxy-2-[(4-methoxybenzenestlfonyl) methyl]-3-(N-benzenecarbonylamino)-propionamide.

2-Hydroxy-2-[(4-methoxybenzenesulfonyl)methyl]-3-(N-benzenecarbonylamino)-propionic acid (0.25 g, 0.63 mmol), 1-(3-dimethylaminopropyl)-3-ethylcarbodiimide hydrochloride (0.24 g, 1.26 mmol), hydroxylamine hydrochloride (0.066 g, 0.95 mmol), and 5 mL of 1-methyl-2-pyrrolidinone are stirred under a nitrogen atmosphere at ambient temperature for 4 hours. Diethyl ether (100 mL) is added, and the mixture is stirred overnight. The ether is decanted from the oily residue. The oil is washed twice more with ether and then chromatographed on silica gel, eluting with 20% hexane and 4% acetic acid in ethyl acetate. The title compound is obtained as a white powder.

$^1$H NMR (MeOD) δ 5 7.87–7.79, 7.55–7.45, 7.09–7.06, 3.88, 3.84–3.55; MS (ES–) 406.9 (M–H); HRMS (EI) calcd for $C_{18}H_{20}N_2O_7S+H_1$ 409.1069, found 409.1076.

EXAMPLE 6

Preparation of N-Hydroxy-2-hydroxy-2-[(4-methoxybenzenesulfonyl) methyl]-3-[N-(cyclopentylcarbonyl)amino]-propionamide

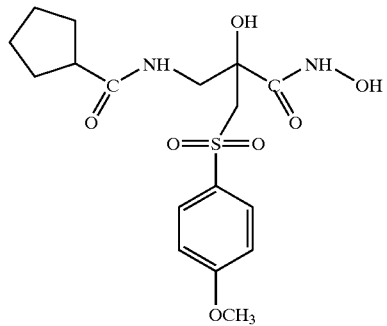

Following the general procedure outlined in EXAMPLE 5 (steps 1 to 3) and making non-critical variations, but starting with cyclopantanecarbonitrile in step 1, in place of benzonitrile, the title compound is obtained as a white solid.

$^1$H NMR (MeOD) δ 7.86–7.83, 7.09–7.06, 3.88, 3.81–3.76, 3.54–3.39, 2.71–2.58, 2.03–1.67; MS (ES+) 401.1 (M+H), (ES–) 399.1 (M–H). HRMS (EI) calcd for $C_{17}H_{24}N_2O_7S +H_1$ 401.1382, found 401.1378.

EXAMPLE 7

Preparation of N-Hydroxy-2-hydroxy-2-[(4-methoxybenzenesulfonyl) methyl]-3-(N-(4-methoxybenzenecarbonyl)amino)-propionamide

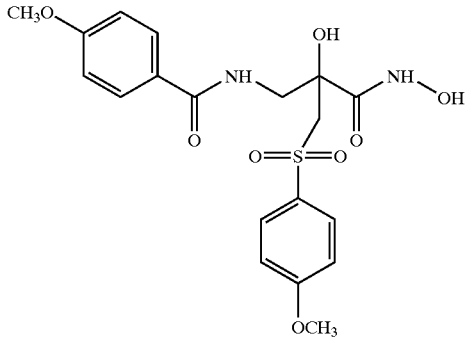

Step 1 Preparation of 2-Hydroxy-2-[(4-methoxybenzenesulfonyl)methyl]-3-(N-(4-methoxybenzenecarbonyl)amino)-propionic Acid.

Following the general procedure outlined in EXAMPLE 5 (steps 1 and 2) and making non-critical variations, but starting with 4-methoxybenzonitrile in step 1, in place of benzonitrile, the title compound is obtained as a white solid after lyophilization from water.

$^1$H NMR (MeOD) δ 7.86–7.83, 7.77–7.74, 7.07–7.06, 6.97–6.94, 3.89–3.87, 3.83, 3.72–3.61; MS (ES+) 423.9 (M+H), (ES–) 421.9 (M–H).

Step 2 Preparation of N-Hydroxy-2-hydroxy-2-[(4-methoxybenzenesulfonyl) methyl]-3-(N-(4-methoxybenzenecarbonyl)amino)-propionamide.

2-Hydroxy-2-[(4-methoxybenzenesulfonyl)methyl]-3-(N-(4-methoxybenzenecarbonyl)amino)-propionic acid (100 mg, 0.24 mmol), 1-(3-dimethylaminopropyl)-3-ethylcarbodiilnide hydrochloride (68 mg, 0.35 mmol), O-tert-butylhydroxylamine hydrochloride (118 mg, 0.944 mmol), and 4-methylmorpholine (131 mg, 0.354 mmol) are dissolved in 20 mL of methylene chloride. The reaction mixture is stirred under nitrogen for 6 hours. The solvent is removed under reduced pressure, and the residue is dissolved in ethyl acetate. The organic layer is washed with 1N sodium hydrogen sulfate, 5% sodium bicarbonate, and saturated brine and dried over magnesium sulfate. The solvent is removed to yield 71 mg of white solid which is recrystallized from methanol. The tert-butyl protecting group is removed by treatment with 50% trifluoroacetic acid in methylene chloride for 24 hours. The solvents are removed, and the crude product is purified by reverse phase chromatography on a C18 Vydac column using a water-acetonitrile elution system to yield the title compound as a white solid.

$^1$H NMR (MeOD) δ 7.87–7.84, 7.80–7.77, 7.09–7.06, 6.99–6.96, 3.88, 3.84, 3.70–3.59; MS (ES+) 438.9 (M+H), (ES–) 436.8 (M–H); HRMS (EI) calcd for $C_{19}H_{22}N_2O_8S +H_1$ 439.1175, found 439.1195.

EXAMPLE 8

Biological Activity Test

Inhibitory activity is evaluated in one or more of the MMP enzymes (stromelysin, gelatinase, and collagenase) in vitro using particle concentration fluorescence assay. An inhibitor binds to MMP enzymes which prevents the degradation of a substrate by stromelysin, gelatinase, or coilagenase. The substrate has attached to it a fluorescein and a biotin moiety. The intact substrate then binds to an avidin-coated particle via the biotin moiety. Once the particle is washed and dried, a fluorescent signal is generated since the fluorescent group is attached to the particle. Without an inhibitor present, the substrate is degraded by MMP enzymes and the fluorescein group is removed, therefore, no fluorescent signal can be detected. Testing compounds are dissolved in DMSO to the desired concentration, then the solutions are diluted to 1:5 with MMP buffer (50 mM Tris-HCl, pH 7.5; 150 mM NaCl; 0.02% $NaN_3$). Serial two-fold dilutions of each compound are prepared. A concentrated, activated enzyme solution is transferred into each plate of the testing compounds, and the mixture is incubated at room temperature for 15 minutes. Thawed MMP substrate is then added into all plates, and the plates are incubated in the dark for 1–3 hours at room temperature. At this point, the substrate mixture is mixed with 0.1% avidin-coated polystyrene particles. After 15 minutes, the fluorescence values are measured following filtration and washing of the beads. Ki values are then calculated. Inhibitory data for the compounds of this invention are shown in TABLE 1. Compounds with lower Ki values are expected to be more effective as MMP inhibitors. It is expected that a compound with a Ki less than 15 μM against stromelysin will display therapeutic effects in connective tissue disorders.
TABLE 1
MMP Inhibition Constants (Ki, $\mu$M) of the Compounds of the Invention
| Example No. | Stromelysin Ki ($\mu$M) | Gelatinase Ki ($\mu$M) |
|---|---|---|
| 1 | 0.074 | 0.0019 |
| 1, Enantiomer A | 0.021 | 0.0085 |
| 1, Enantiomer B | 0.080 | 0.00034 |
| 2 | 0.18 | 0.031 |
| 3 | 0.046 | 0.013 |
| 4 | 0.039 | 0.0075 |
| 5 | 0.24 | 0.023 |
| 6 | 0.35 | 0.070 |
| 7 | 0.28 | 0.017 |
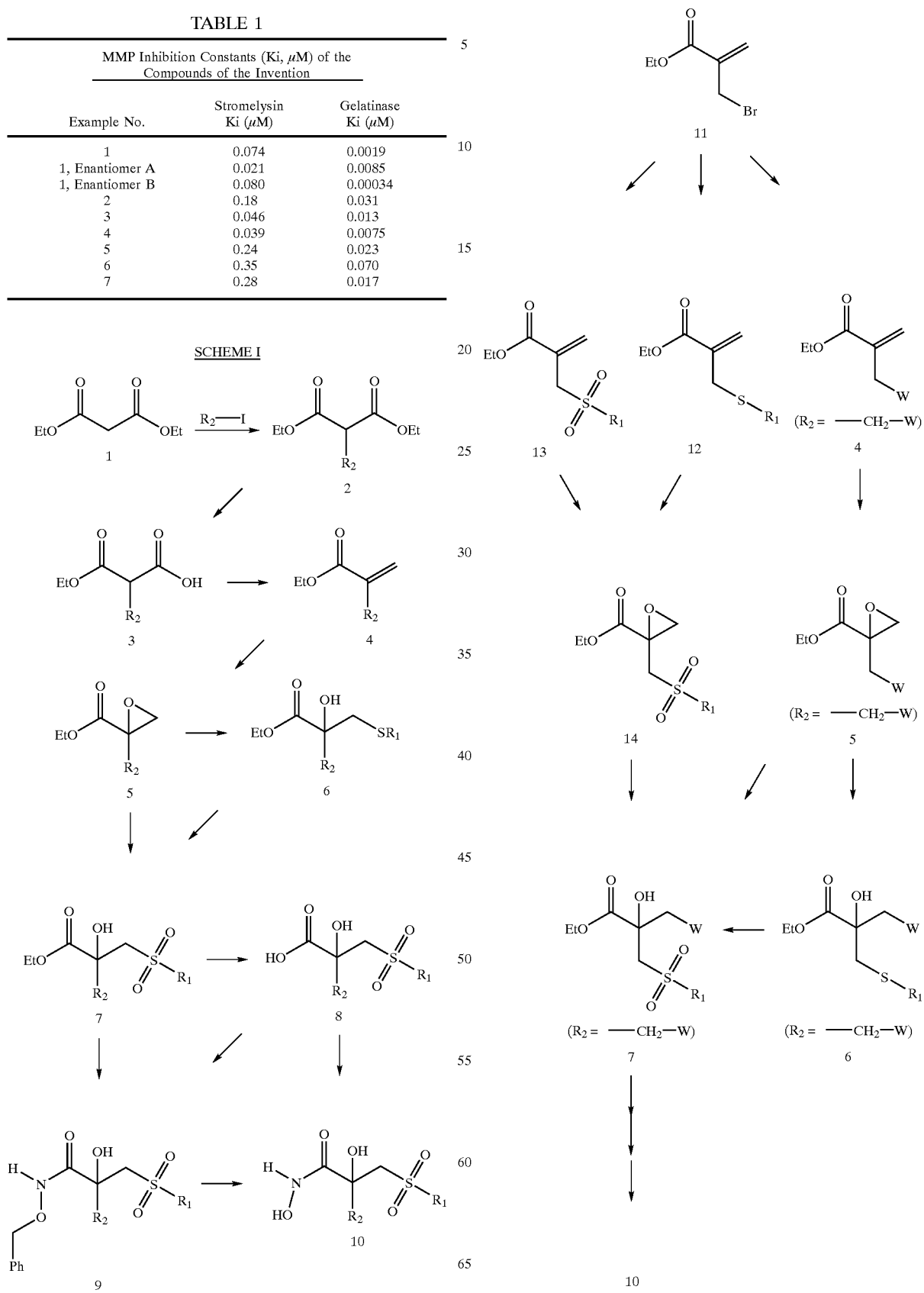

SCHEME III
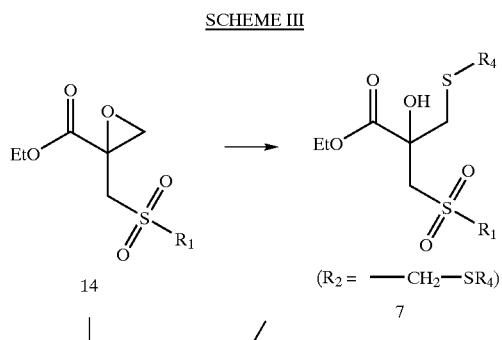
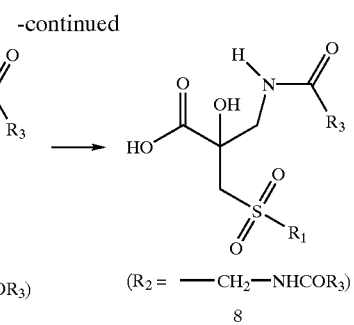
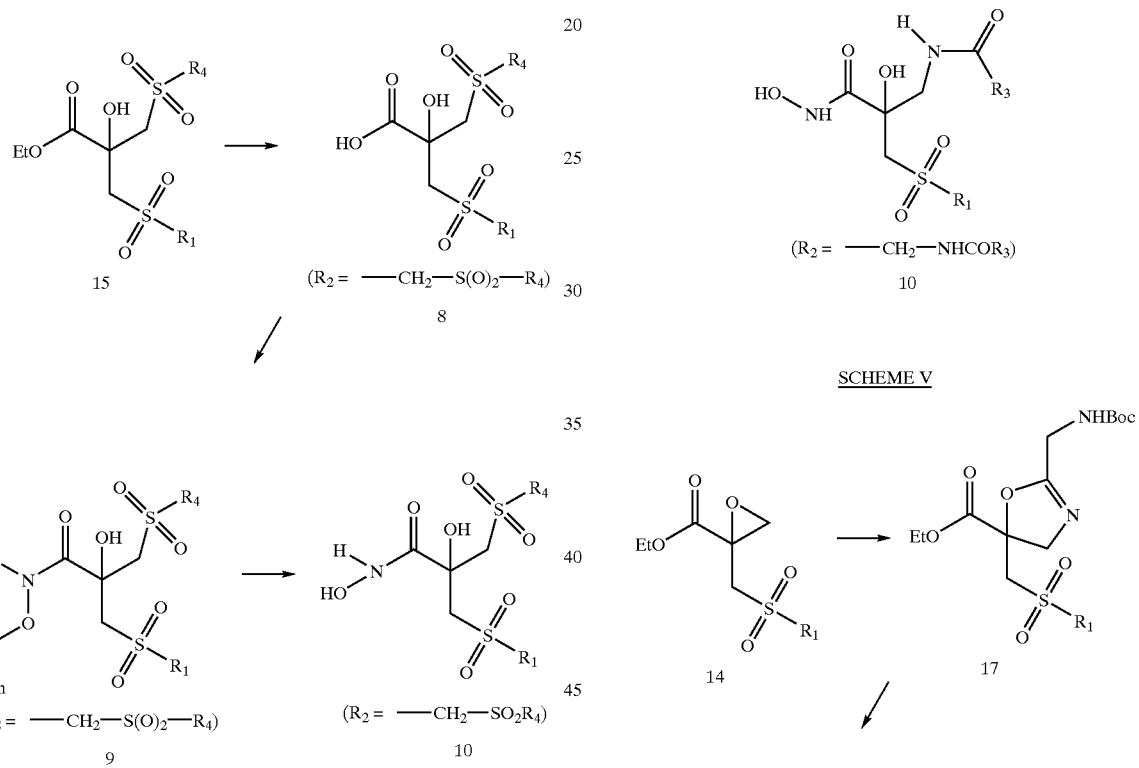
SCHEME IV
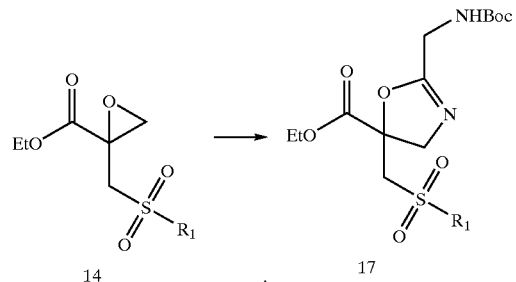
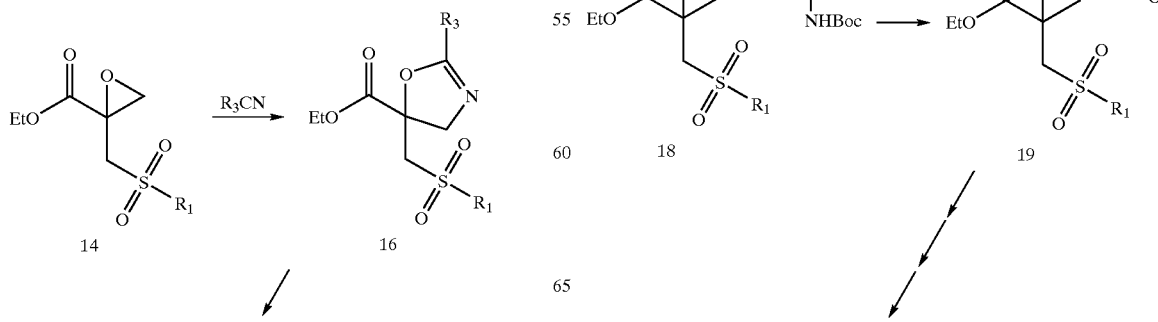

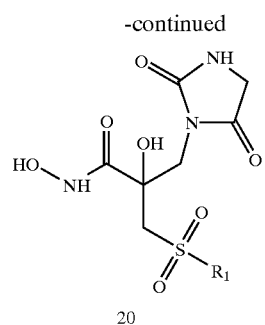

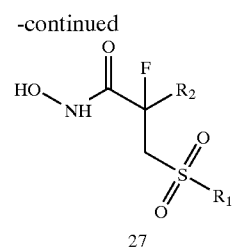

U.S. Provisional Application Serial No. 60/072,655, filed on Nov. 21, 1997, is incorporated herein by reference.

We claim:

1. A compound which is
2-Hydroxy-2-(phenylthio)methyl-3-(4-butoxybenzenesulfonyl)propionic acid;
2-Hydroxy-2-(benzylthio)methyl-3-(4-butoxybenzenesulfonyl)propionic acid;
2-Hydroxy-2-(2-benzylthio-2-methylethyl)-3-(4-butoxy-benzenesulfonyl)propionic acid;
2-Hydroxy-2-(phenylthio)methyl-3-(4-chlorobiplenyl-sulfonyl)propionic acid;
2-Hydroxy-2-(benzylthio)methyl-3-(4-chlorobiphenyi-sulfonyl)propionic acid;
2-Hydroxy-2-(2-benzylthio-2-methylethyl)-3-(4-chloro-biphenylsulfonyl)propionic acid;
2-Hydroxy-2-(phenylthio)methyl-3-(4-phenoxybenzene-sulfonyl)propionic acid;
2-Hydroxy-2-(benzylthio)methyl-3-(4-phenoxybenzene-sulfonyl)propionic acid;
or a pharmaceutically acceptable salt thereof.

2. A compound having the following formula 8:

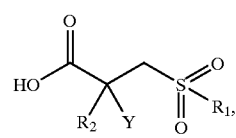

wherein
$R_2$ is $CH_2$—S—$C_6H_6$
$R_1$ is $C_6H_6$—$C_6H_6$—Cl
Y is OH;
or a pharmaceutically acceptable salt thereof.

3. A pharmaceutical composition comprising the compound of claim 1 and a pharmaceutically acceptable carrier.

4. A pharmaceutical composition comprising the compound of claim 2 and a pharmaceutically acceptable carrier.

5. A method of treating a human suffering from or susceptible to diseases involving connective tissue degradation comprising administering to a patient in need thereof an effective amount of a compound having the following formula 8:

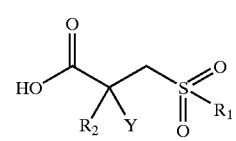

SCHEME VI

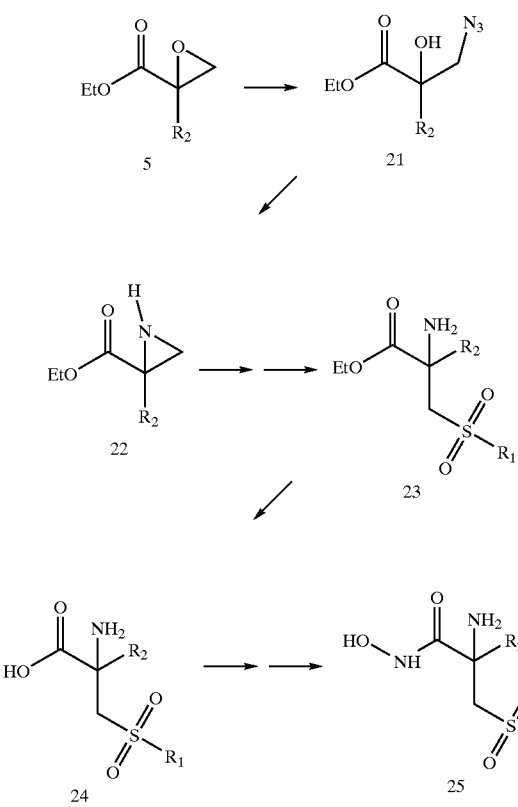

SCHEME VII

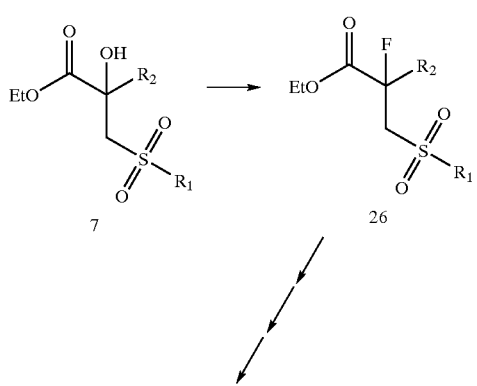

or a pharmaceutically acceptable salt, wherein $R_1$ is
- a) $C_{4-12}$ alkyl,
- b) $C_{4-12}$ alkenyl,
- c) $C_{4-12}$ alkynyl,
- d) —$(CH_2)_h$—$C_{3-8}$ cycloalkyl,
- e) —$(CH_2)_h$-aryl,
- f) —$(CH_2)_h$-aryl substituted with $C_{1-4}$ alkyl, $C_{1-4}$ alkoxy, phenyl, phenoxy, —$NO_2$, —$CF_3$, —CN, or —$N(C_{1-4}$ alkyl$)_2$, $R_2$ is
- a) $C_{1-12}$ alkyl,
- b) $C_{1-12}$ alkyl substituted with one to three halo, —CH, —$NO_2$, —$CF_3$, —$N(R_3)_2$, —$SR_3$, or OH,
- c) $C_{2-12}$ alkenyl,
- d) $C_{2-12}$ alkenyl substituted with one to three halo, —CH, —$NO_2$, or —$CF_3$,
- e) $C_{2-12}$ alkynyl,
- f) $C_{2-12}$ alkynyl substituted with one to three halo, —CN, —$NO_2$, or —$CF_3$,
- g) —$(CH_2)_h$—$C_{3-8}$ cycloalkyl,
- h) —$(CH_2)_h$—$C_{3-8}$ cycloalkyl substituted with one to three $C_{1-4}$ alkyl, $C_{1-4}$ alkoxy, or halo,
- i) —$(CH_2)_h$—$C_{3-8}$ cycloalkenyl,
- j) —$(CH_2)_h$—$C_{3-8}$ cycloalkenyl substituted with one to three $C_{1-4}$ alkyl, $C_{1-4}$ alkoxy, or halo,
- k) —$(CH_2)_h$-aryl,
- l) —$(CH_2)_h$-aryl substituted with one to three $C_{1-4}$ alkyl, $C_{1-4}$ alkoxy, —$CF_3$—OH, —$NO_2$, —CN, —$N(R_3)_2$, —$SR_3$, —$SO_2(C_{1-4}$ alkoxy), —$C(=O)R_3$, or —$NC(=O)R_3$,
- m) —$(CH_2)_h$-aryl substituted with one to five halo,
- o) —$(CH_2)_i$—X—$R_4$, optionally the —$(CH_2)_i$-chain can be substituted with one or two $C_{1-4}$ alkyl or phenyl, which in turn can be substituted with one to three halo or $C_{1-4}$ alkyl, or
- p) —$(CH_2)_h CHR_5 R_6$;

$R_3$ is
- a) H,
- b) $C_{3-6}$ cycloalkyl,
- c) $C_{1-4}$ alkyl,
- d) —$(CH_2)_h$-phenyl, or
- e) —$(CH_2)_h$-phenyl substituted with one to three $C_{1-4}$ alkyl, $C_{1-4}$ alkoxy, or halo;

X is
- a) —O—,
- b) —$S(=O)_j$—,
- c) —$NR_7$—,
- d) —$S(=O)_2 NR_8$—, or
- e) —C(=O)—;

$R_4$ is
- a) H,
- b) $C_{1-8}$ alkyl,
- c) —$(CH_2)_h$-phenyl,
- d) —$(CH_2)_h$-phenyl substituted with one to three $C_{1-4}$ alkyl, $C_{1-4}$ alkoxy, phenyl, phenoxy, halo, —$NO_2$, or —CN;

$R_5$ is
- a) —$C_{1-4}$ alkyl, or
- b) —$C(=O)R_3$;

$R_6$ is
- a) —$C(=O)R_3$, or
- b) —$(CH_2)_h C(=O)R_3$;

$R_7$ is
- a) H,
- b) $C_{1-4}$ alkyl,
- c) —$(CH_2)_h$-phenyl,
- d) —$(CH_2)_h$-phenyl substituted with one to three $C_{1-4}$ alkyl, $C_{1-4}$ alkoxy, or halo,
- e) —C(=O)—$R_3$,
- f) —$S(=O)_2 R_3$, or
- g) —$C(=O)OR_3$;

$R_8$ is
- a) $C_{1-4}$ alkyl,
- b) —$(CH_2)_h$-phenyl, or
- c) —$(CH_2)_h$-phenyl substituted with one to three $C_{1-4}$ alkyl, $C_{1-4}$ alkoxy, or halo;

Y is
- a) —OH,
- b) fluoro;

$R_9$ and $R_{10}$ are the same and different and are
- a) H,
- b) —C(=O)—$R_3$,
- c) —C(=O)—$OR_3$, or
- d) —C(=O)—$NHR_3$;

aryl is monocarbocyclic, or bicarbocyclic aromatic moiety;

h) is 0, 1, 2, 3, 4, 5, or 6; and i is 1, 2, 3, 4, 5, 6, 7, 8,9, or 10, and wherein said diseases are selected from the group consisting of osteoarthritis, rheumatoid arthritis, septic arthritis, osteopenias, osteoporosis, periodontitis, gingivitis, corneal ulceration, dermal ulceration, gastriculceration, and asthma.

6. The method of claim 5, wherein said compound is administered orally, parenterally, or topically.

7. The method of claim 5, wherein said effective amount is from 0.1 to 100 mg/kg of body weight per day.

8. A method of treating a human suffering from or susceptible to diseases involving connective tissue degradation comprising administering to a patient in need thereof an effective amount of the compound of claim 2, wherein said diseases are selected from the group consisting of osteoarthritis, rheumatoid arthritis, septic arthritis, osteopenias, osteoporosis, periodontitis, gingivitis, corneal ulceration, dermal ulceration, gastric ulceration, and asthma.

9. The method of claim 8, wherein said compound is administered orally, parenterally, or topically.

10. The method of claim 8, in said effective amount is from 0.1 to 100 mg/kg of body weight per day.

11. A method of treating a human suffering from or susceptible to diseases involving connective tissue degradation comprising administering to a patient in need thereof an effective amount of the compound of claim 1, wherein said diseases are selected from the group consisting of osteoarthritis, rheumatoid arthritis, septic arthritis, osteopenias, osteoporosis, periodontitis, gingivitis, corneal ulceration, dermal ulceration, gastric ulceration, and asthma.

12. The method of claim 11, wherein said compound is administered orally, parenterally, or topically.

13. The method of claim 11, wherein said effective amount is from 0.1 to 100 mg/kg of body weight per day.

* * * * *

UNITED STATES PATENT AND TRADEMARK OFFICE
CERTIFICATE OF CORRECTION

PATENT NO. : 6,437,177 B1
DATED : August 20, 2002
INVENTOR(S) : Warpehoski et al.

It is certified that error appears in the above-identified patent and that said Letters Patent is hereby corrected as shown below:

<u>Title page,</u>
Items [76] and [73] should read:

-- [76]  Inventors:     Martha A. Warpehoski, Portage;
                        Mark Allen Mitchell, Kalamazoo;
                        Donald E. Harper, Plainwell;
                        Linda Louise Maggiora, Kalamazoo;
                        all of MI (US) --

-- [73]  Assignee:      Pharmacia & Upjohn Company,
                        Kalamazoo, MI (US) --

Signed and Sealed this

Eighteenth Day of March, 2003

JAMES E. ROGAN
*Director of the United States Patent and Trademark Office*